United States Patent
Kestler et al.

[11] Patent Number: 6,148,225
[45] Date of Patent: Nov. 14, 2000

[54] ULTRASOUND THERAPY APPARATUS AND METHOD FOR OPERATING SAME DURING MR MONITORING

[75] Inventors: Joachim Kestler, Pinzberg; Ulrich Schaetzle, Roettenbach; Erhard Schmidt, Selb, all of Germany

[73] Assignee: Siemens Aktiengesellschaft, Munich, Germany

[21] Appl. No.: 09/161,134

[22] Filed: Sep. 25, 1998

[30] Foreign Application Priority Data

Sep. 25, 1997 [DE] Germany .......................... 197 42 379

[51] Int. Cl.[7] .................................................. A61B 5/055
[52] U.S. Cl. ................................................. 600/411; 601/3
[58] Field of Search .......................... 601/3, 2; 600/411, 600/437

[56] References Cited

U.S. PATENT DOCUMENTS

| | | | |
|---|---|---|---|
| 5,307,812 | 5/1994 | Hardy et al. | 128/653.2 |
| 5,323,779 | 6/1994 | Hardy et al. | 128/653.2 |
| 5,415,163 | 5/1995 | Harms et al. | 128/653.2 |
| 5,443,068 | 8/1995 | Cline et al. | 128/653.5 |
| 5,485,839 | 1/1996 | Aida et al. | 128/653.1 |
| 5,492,122 | 2/1996 | Button et al. | 128/653.2 |
| 5,590,653 | 1/1997 | Aida et al. | 128/653.2 |
| 5,938,600 | 8/1999 | Van Vaals et al. | 600/411 |

FOREIGN PATENT DOCUMENTS

| | | |
|---|---|---|
| 0 534 607 | 3/1993 | European Pat. Off. . |
| 43 11 327 | 10/1994 | Germany . |

*Primary Examiner*—Marvin M. Lateef
*Assistant Examiner*—Eleni Mantis Mercader
*Attorney, Agent, or Firm*—Hill & Simpson

[57] ABSTRACT

In an ultrasound therapy apparatus and a method for the operation of an ultrasound therapy apparatus, a high-frequency generator generates electrical signals with different discrete frequency values that lie within a first frequency band in chronological succession. Whole multiples of the discrete frequency values do not lie in a second frequency band that corresponds to the reception band of a simultaneously operated diagnostic magnetic resonance apparatus.

5 Claims, 2 Drawing Sheets

ULTRASOUND THERAPY APPARATUS AND METHOD FOR OPERATING SAME DURING MR MONITORING

BACKGROUND OF THE INVENTION

1. Field of the Invention

The present invention is directed to a method for the operation of an ultrasound therapy apparatus of the type, wherein a high-frequency generator generates an electrical signal that is time-variable in frequency, and the signal is supplied via a transmission amplifier to an ultrasound transducer arrangement.

The invention is also directed to an ultrasound therapy apparatus of the type having a high-frequency generator that is connected to an ultrasound transducer arrangement via a transmission amplifier.

2. Description of the Prior Art

In order to avoid skin burns, local acoustic field elevations in the application region are neutralized by wobbling the therapy frequency within a frequency band, as disclosed in the German OS 43 11 327. The therapy frequency is steadily varied between an upper and lower limit frequency, so that secondary maxima in the acoustic field are steadily spatially displaced. Given longer application at a constant location, the secondary maxima cause skin burns. European Application 0 534 607 discloses an apparatus wherein heat therapy of tumors can be implemented with focused ultrasound within a magnetic resonance apparatus.

When a diagnostic magnetic resonance apparatus is operated simultaneously with an ultrasound therapy apparatus, for example for monitoring the progress of the therapy, the operation of the ultrasound therapy apparatus leads to disturbances in the magnetic resonance image because harmonics of the therapy frequency couple into the high-frequency reception channel. Fast magnetic resonance sequences with a reception bandwidth of up to ±200 kHz are particularly very sensitive with respect to noise emissions. Only a non-simultaneous operation of the ultrasound therapy apparatus with the magnetic resonance apparatus is then possible. Therapy monitoring with the magnetic resonance apparatus thus is greatly restricted.

SUMMARY OF THE INVENTION

An object of the present invention is to provide a method for the operation of an ultrasound therapy apparatus that does not negatively affect the imaging of the magnetic resonance apparatus. It is also an object of the present invention to provide an ultrasound therapy apparatus that does not negatively affect a magnetic resonance imaging given simultaneous operation.

The first object is achieved in a method wherein high-frequency electrical signals are generated in chronological succession with different discrete frequency values that lie within a first frequency band, and wherein whole multiples of the discrete frequencies do not lie in a second frequency band that corresponds to the reception band of a simultaneously operated diagnostic magnetic resonance apparatus. The therapy frequencies are thereby switched rapidly compared to the heating process of the tissue. With such an operating method, an ultrasound therapy apparatus can be operated simultaneously with a diagnostic magnetic resonance apparatus, enabling direct monitoring of the therapy with the assistance of the diagnostic magnetic resonance apparatus. Local intensity elevations in the ultrasound field that could possibly lead to local skin bumrs given longer activation are precluded by the shifts due to th e different therapy frequencies. The intensity of the acoustic field is therefore more uniformly distributed over the entire time duration of the therapy and the risk for the patient is clearly reduced.

The different frequency signals will have harmonics at a maximum distance from the tuned reception bandwidth of the diagnostic magnetic resonance apparatus in an embodiment of the method wherein the different frequencies are determined by dividing down an initial frequency with odd-numbered divisors, with an initial frequency which amounts to twice a center frequency of the reception bandwidth.

The latter object relating to an ultrasound therapy apparatus that operates according to the inventive method is achieved in such an apparatus having a high-frequency generator with an oscillator that is connected to at least two frequency dividers, the frequency dividers each having an output connected to a switch matrix for selectively electrically connecting one of the frequency dividers to the transmission amplifier.

DESCRIPTION OF THE PREFERRED EMBODIMENTS

Figure 1:
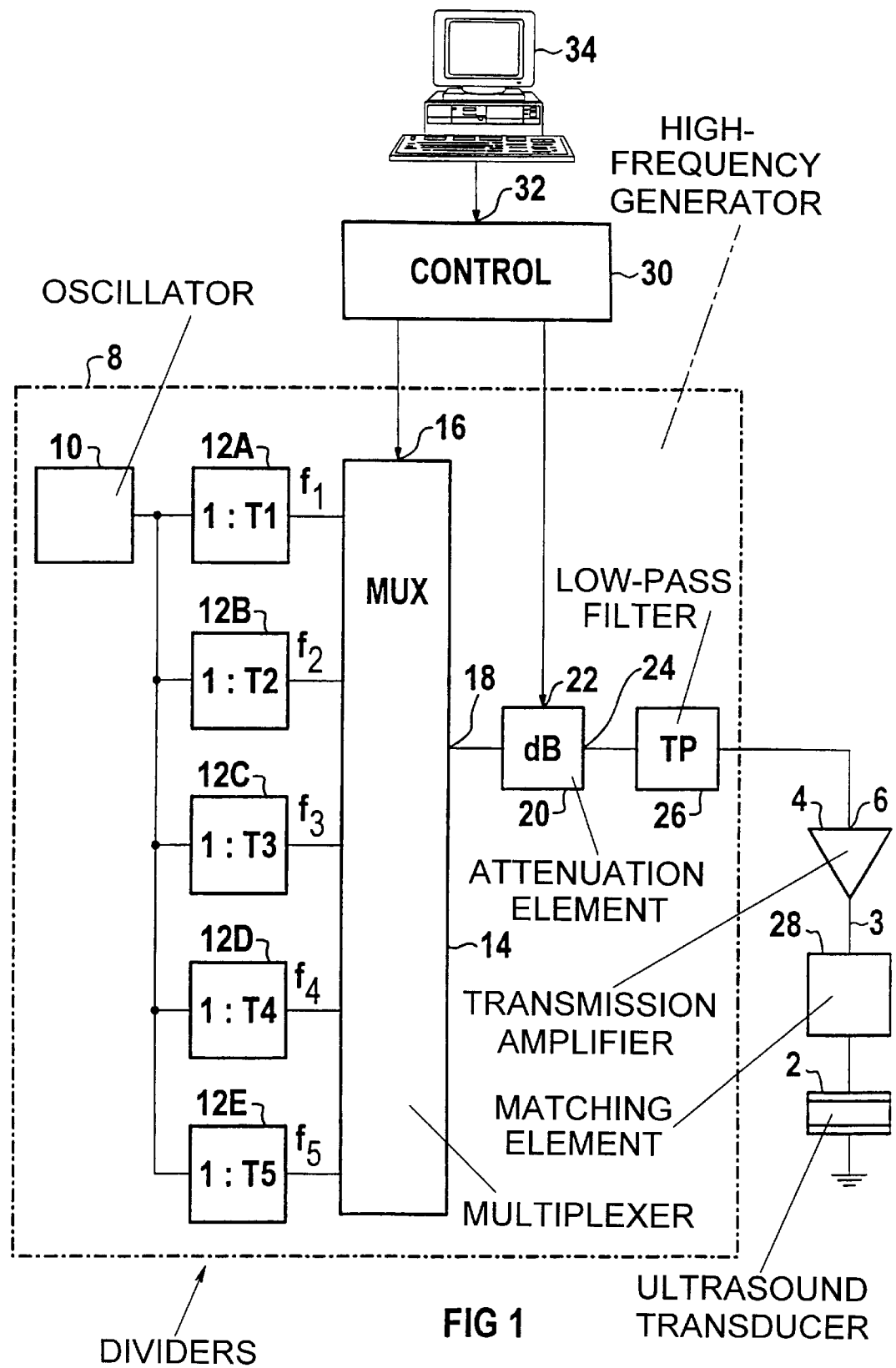
FIG. 1 is a block circuit diagram of an ultrasound therapy apparatus whose operation does not negatively affect a magnetic resonance imaging, constructed and operating in accordance with the principles of the present invention.

FIG. 1 shows the components of an ultrasound therapy apparatus that enable of disturbance-free operation together with a diagnostic magnetic resonance apparatus in a block circuit diagram. The ultrasound therapy apparatus has an ultrasound transducer 2 that can be applied to a skin surface or to an organ surface for therapy. During therapy, high-power ultrasound signals focused in the MHZ range are emitted into the tissue in order to effect a local temperature elevation in the tissue in the region of the focus. The ultrasound transducer 2 is driven via a feed cable 3 by a transmission amplifier 4 that amplifies a low-power control signal supplies at its input 6 for transmission. By contrast to conventional ultrasound apparatus, the control signal supplied to the input 6 is not steadily varied in frequency; rather, the control signal assumes different discrete frequency values in chronological succession that lie within the operable bandwidth of the ultrasound transducer 2. The frequencies are rapidly switched compared to the heating process in the tissue in order to avoid local heating, particularly in the application region of the ultrasound transducer 2 at the skin. The switching in the inventive method and apparatus is typically 2 through 5 times per second compared to a heating rate from 37° C. to 60° C. through 90° C. within an acoustic irradiation duration of 10 seconds.

The discrete frequencies are generated by a high-frequency generator 8. The structure and the dimensioning of the high-frequency generator 8 are determined by the operating frequency of the magnetic resonance apparatus, including the reception bandwidth. The following description assumes a magnetic resonance apparatus with a 1.5 Tesla basic magnetic field, as a result of which a magnetic resonance frequency of 63.5 MHZ derives as the operating frequency. The gradient fields required in the magnetic resonance apparatus shift the magnetic resonance signals in a frequency range of $\Delta f_{MR}=\pm 200$ kHz, so that the lower limit frequency of the magnetic resonance apparatus amounts to 63.3 MHZ and the upper limit frequency of the magnetic resonance apparatus amounts to 63.7 MHZ. An oscillator 10 belonging to the high-frequency generator 8 of the therapy apparatus oscillates constantly on a frequency that corresponds to twice the center frequency of the reception range of the magnetic resonance apparatus, i.e. 127 MHZ in this example. This master frequency is supplied in parallel to five frequency dividers 12A through 12E that divide down the master frequency generated by the oscillator 8 in odd-numbered fashion. The dividers 12A–12E are selected such that the divided-down frequency lies within the operating bandwidth of the ultrasound transducer 2.

It is assumed in this example that the operating frequency of the ultrasound transducer amounts to $2 \cdot f_{ous}=1.7$ MHZ with a bandwidth of $\Delta f_{us}=\pm 0.1$ MHZ. The divisor values for the frequency dividers 12A through 12E are thus defined. The frequency divider 12A divides the master frequency down with a divisor T1=79, the frequency divider 12B with a divisor T2=77, the frequency divider 12C with a divisor T3=75, the frequency divider 12D with a divisor T4=73, and the frequency divider 12E with a divisor T5=71.

The outputs of the frequency dividers 12A through 12E are connected to the inputs of a switch matrix in the form of a multiplexer 14 that connects one of the frequency dividers 12A through 12E at a time to its output 18, dependent on a control signal at its control input 16. A following attenuation element 20 regulates the signal amplitude at its output 24 dependent on a control signal at its control input 22. A low-pass filter 26 follows in the signal chain, this only allowing the fundamental wave parts of the divided-down frequencies $f_1$ through $f_5$ to pass, so that a sinusoidal signal is supplied as the control signal at the input 6 of the transmission amplifier 4. A matching element 28 serves for matching the ultrasound transducer 2 to the impedance of the feeder cable 3. An executive sequence controller 30 that effects the ongoing switching of the frequency dividers 12A through 12E and determines the applied power supplies the control signals at the control inputs 16 and 22. The controller 30 is programmed at its control input 32 by an operating console 34.

Figure 2:
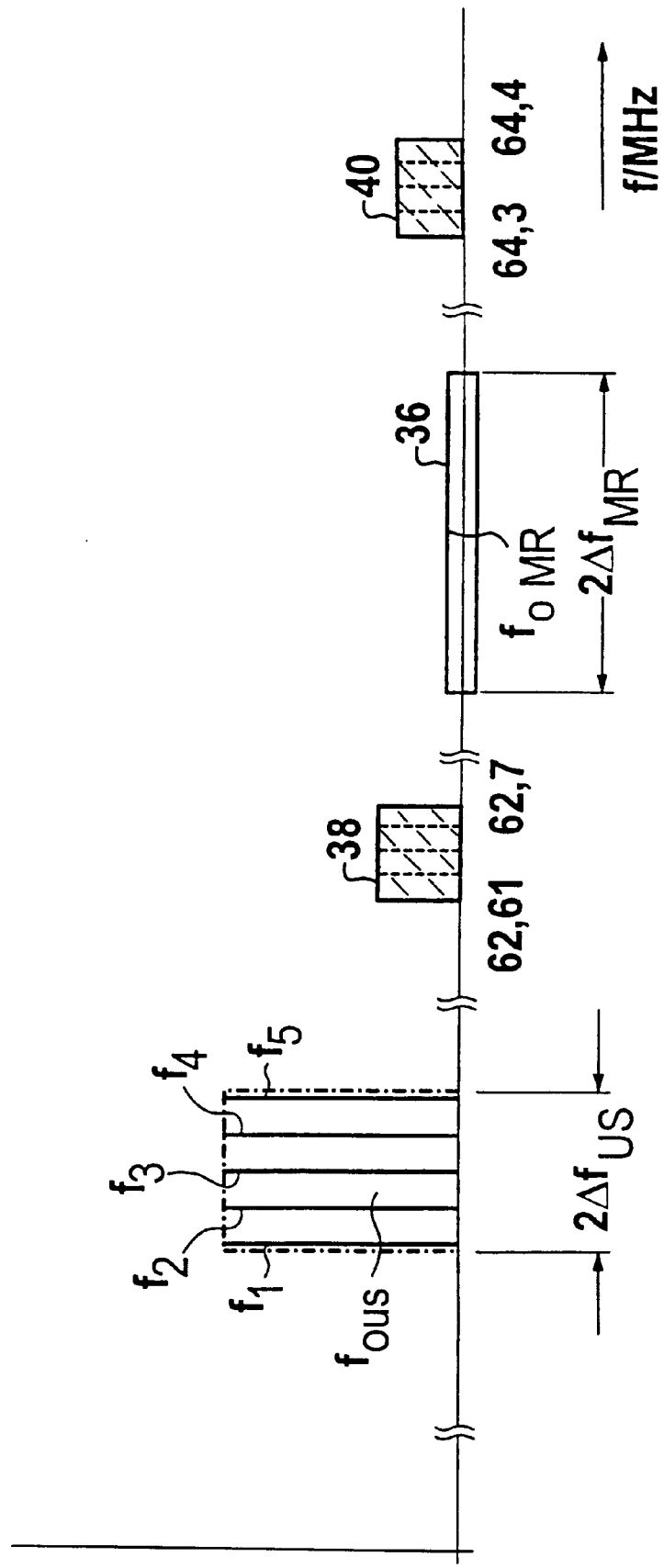
FIG. 2 is a frequency diagram showing the position of the therapy frequencies of the ultrasound therapy apparatus of FIG. 1 with corresponding harmonics.

In a frequency diagram, FIG. 2 shows the position of the individual frequencies. The sensitivity region 36 or the reception band of the magnetic resonance apparatus is characterized by the center frequency $f_{OMR}=63.5$ MHZ and the bandwidth $\Delta f_{MR}=\pm 200$ kHz. The therapy frequencies emitted by the ultrasound apparatus in chronological succession have the frequencies $f_1$ through $f_5$ that derive from twice the working frequency of the magnetic resonance apparatus $2 \, f_{OMR}$ by a corresponding odd-numbered division. Here, the ultrasound therapy apparatus can emit a total of five discrete ultrasound frequencies $f_1$ through $f_5$ in chronological succession. The following table indicates the therapy frequencies $f_1$ through $f_5$ generated in the ultrasound therapy apparatus and harmonics that lie in the region of the working frequency of the magnetic resonance apparatus. The frequencies are recited in MHZ.

| Fundamental wave | $f_1 = 1.608$ | $f_2 = 1.649$ | $f_3 = 1.693$ | $f_4 = 1.74$ | $f_5 = 1.789$ |
|---|---|---|---|---|---|
| 35th harmonic |  |  |  |  | 62.615 |
| 36th harmonic |  |  |  | 62.64 | 64.404 |
| 37th harmonic |  |  | 62.641 | 64.38 |  |
| 38th harmonic |  | 62.662 | 64.334 |  |  |
| 39th harmonic | 62.712 | 64.311 |  |  |  |
| 40th harmonic | 64.32 |  |  |  |  |

With the selected divisors $T_1$ through $T_5$, the harmonics of the therapy frequencies $f_1$ through $f_5$ have a maximum distance from the sensitivity region 36 of the magnetic resonance apparatus. Symbolized by a first diagonally hatched region 38, the 35$^{th}$ harmonic of the therapy frequency $f_5$, the 36$^{th}$ harmonic of the therapy frequency $f_4$, the 37$^{th}$ harmonic of the therapy frequency $f_3$, the 38$^{th}$ harmonic of the therapy frequency $f_2$ and 39$^{th}$ harmonic of the therapy frequency $f_1$ lie in close proximity to one another below the sensitivity region 36 of the magnetic resonance apparatus. Symbolized by a second diagonally hatched region 40, the 36$^{th}$ harmonic of the therapy frequency $f_5$, the 37$^{th}$ harmonic of the therapy frequency $f_4$, the 38$^{th}$ harmonic of the therapy frequency $f_3$, the 39$^{th}$ harmonic of the therapy frequency $f_2$ and the 40$^{th}$ harmonic of the therapy frequency $f_1$ lie above the sensitivity region 36 of the magnetic resonance apparatus.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating an ultrasound therapy apparatus during simultaneous operation of a diagnostic magnetic resonance apparatus, said diagnostic magnetic resonance apparatus operating in a magnetic resonance apparatus frequency band, said method comprising the steps of:

supplying high-frequency electrical signals which are chronologically variable in frequency via a transmission amplifier to an ultrasound transducer arrangement for causing said ultrasound transducer arrangement to emit ultrasound; and generating said high-frequency electrical signals with respectively different discrete frequency values within an ultrasound arrangement frequency band in chronological succession, said discrete frequency values comprising whole-number multiple harmonics which are not in said magnetic resonance apparatus frequency band.

2. A method as claimed in claim 1 comprising the step of producing said respectively different discrete frequency values by dividing down an initial frequency with a plurality of odd-numbered divisors, said initial frequency comprising twice a center frequency of said magnetic resonance apparatus frequency band.

3. A method for administering therapy to a subject while simultaneously monitoring progress of said therapy, comprising the steps of:

administering ultrasound therapy to a subject by emitting high-frequency electrical signals which are chronologically variable in frequency via a transmission amplifier to an ultrasound transducer arrangement and emitting ultrasound into said subject from said ultrasound transducer arrangement as ultrasound therapy;

monitoring progress of said ultrasound therapy by magnetic resonance imaging employing a magnetic resonance imaging apparatus having a magnetic resonance apparatus frequency band associated therewith; and generating said electrical signals with respectively different discrete frequency values within an ultrasound transducer arrangement frequency band in chronological succession, and with whole-number multiple harmonics of said discrete frequency values outside of said magnetic resonance apparatus frequency band.

4. A method as claimed in claim 3 comprising the step of producing said respectively different discrete frequency values by dividing down an initial frequency with a plurality of odd-numbered divisors, said initial frequency comprising twice a center frequency of said magnetic resonance apparatus frequency band.

5. An ultrasound therapy apparatus for use in a magnetic resonance imaging apparatus operating in a magnetic resonance apparatus frequency band, said ultrasound therapy apparatus comprising:

an ultrasound transducer arrangement;

a high-frequency generator connected to said ultrasound transducer arrangement via a transmission amplifier for supplying high-frequency electrical signals to said ultrasound transducer arrangement which are chronologically variable in frequency; and said high-frequency generator comprising an oscillator connected to at least two frequency dividers, each frequency divider having an output connected to a switch matrix for selectively electrically connecting one of said frequency dividers at a time to an input of said transmission amplifier, for generating a plurality of respectively different discrete frequency values within an ultrasound transducer arrangement frequency band in chronological succession, having whole-number multiple harmonics which are outside of said magnetic resonance apparatus frequency band.

* * * * *